United States Patent
Montoya et al.

(10) Patent No.: US 10,799,435 B1
(45) Date of Patent: *Oct. 13, 2020

(54) SKIN-TIGHTENING COMPOSITION

(71) Applicant: L'OREAL, Paris (FR)

(72) Inventors: Mariana Montoya, Berkeley Heights, NJ (US); Nicole Burkhard, Ledgewood, NJ (US); David Chan, Edison, NJ (US); Maggie Su, Cranford, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/398,686

(22) Filed: Apr. 30, 2019

(51) Int. Cl.
| A61K 8/06 | (2006.01) |
| A61K 8/25 | (2006.01) |
| A61K 8/73 | (2006.01) |
| A61Q 19/08 | (2006.01) |
| A61K 8/26 | (2006.01) |
| A61K 8/34 | (2006.01) |
| A61K 8/96 | (2006.01) |

(52) U.S. Cl.
CPC ............ A61K 8/062 (2013.01); A61K 8/25 (2013.01); A61K 8/26 (2013.01); A61K 8/345 (2013.01); A61K 8/731 (2013.01); A61K 8/965 (2013.01); A61Q 19/08 (2013.01)

(58) Field of Classification Search
CPC ... A61K 8/06; A61K 8/25; A61K 8/73; A61K 8/28; A61K 8/34; A61K 8/86; A61Q 19/08
See application file for complete search history.

(56) References Cited

U.S. PATENT DOCUMENTS

| 4,255,416 A | 3/1981 | Gillespie |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,100,660 A | 3/1992 | Hawe et al. |
| 6,060,547 A * | 5/2000 | Canter ................. A61K 8/06 424/401 |
| 7,192,599 B2 | 3/2007 | Mercier et al. |
| 9,095,543 B2 | 8/2015 | Susak et al. |
| 2013/0189332 A1 | 7/2013 | Breyfogle |
| 2013/0195783 A1 | 8/2013 | Breyfogle |
| 2014/0356302 A1 | 12/2014 | Yuen |
| 2015/0016862 A1 | 1/2015 | Guay et al. |
| 2015/0037380 A1 | 2/2015 | Newman et al. |
| 2017/0189288 A1 | 7/2017 | Choiu et al. |
| 2017/0189298 A1 | 7/2017 | Manning et al. |
| 2017/0189299 A1 | 7/2017 | Manning et al. |
| 2017/0189320 A1 | 7/2017 | Chiou et al. |
| 2019/0105254 A1 | 4/2019 | Montoya et al. |

FOREIGN PATENT DOCUMENTS

| EP | 228 868 A2 | | 7/1987 |
| EP | 2221045 | * | 8/2010 |
| EP | 2 404 642 A2 | | 1/2012 |
| WO | 2013/109850 A2 | | 7/2013 |

OTHER PUBLICATIONS

"Instantly Ageless," https://instantlyageless.com/?ref=399.
"Serious Skincare Firma-Face XR All Over Skin Tightener," https://www.amazon.com/Serious-Skin-Care-FirmA-Face-Pack/dp/B006YV74WQ/ref=sr_1_5?.
"Peter Thomas Roth Instant Firm Temporary Face Tightener," https://www.amazon.com/Peter-Thomas-Roth-Temporary-Tightener/dp/B0040QG46E/ref=sr_1_2?gclid=EAlaIQobChMIgKugwuyY4glVilMNCh3pswIjEAAYAiAAEgLUj_D_BwE&hvadid=177564892312&hvdev=c&hvlocphy=9061285&hvnetw=g&hvpos=1t2&hvqmt=e&hvrand=11991968898388439064&hvtargid=kwd-24911916416&hydad.
"Fusion Beauty Nip Line Erase Instant Line Remover," https://www.amazon.com/d/Face-Concealers-Neutralizers/Fusion-Beauty-Erase-Instant-Eraser/B005EKIRD8.
"Hydroxatone 90 Second Wrinkle Reducer," https://www.amazon.com/Hydroxatone-Second-Wrinkle-Reducer-0-33/dp/B06XD31CVL/ref=sr_1_3?gclid=EAlaIQobChMIp4ixm-6Y4glViVcNCh25kg3OEAAYAiAAEgIPM_D_BwE&hvadid=177563170535&hvdev=c&hvlocphy=9061285&hvnetw=g&hvpos=1t2&hvqmt=b&hvrand=12675985482290955293&hvtargid=kwd-11327718275&hyda.
"NuNutrients Facelift," https://www.amazon.com/Nunutrients-Facelift-Aging-Serum-Mixed/dp/B00TKKMIRO.
"Renoir No Lines Temporary Wrinkle Remover," https://www.amazon.com/Renoir-Lines-Temporary-Wrinkle-Remover/dp/B0019W29DO.
"Vecua Enrich Honey Moisture Pack," https://www.adorewe.com/product/vecua-honey-wonder-honey-honey-dew-extra-pack-in-bath-yuzu-and-honey-200ml_39921607.
"Bare Skin," https://www.bareminerals.com/skincare/all-skincare/.
"L'Oreal Paris Miracle Eye Blur," https://www.ebay.com/i/263428144627?chn=ps.

* cited by examiner

Primary Examiner — Shirley V Gembeh
(74) Attorney, Agent, or Firm — Polsinelli PC

(57) ABSTRACT

Skin-tightening compositions and methods for using the same, which provide a long-lasting skin-tightening effect and a mattifying finishing effect are described. The skin-tightening composition may be in the form of an oil-in-water emulsion and comprise one or more polyvalent silicates; one or more cellulose thickeners; one or more clays selected from hectorite and organically modified hectorites; one or more polysaccharide film forming agents; one or more polyols; one or more acrylate polymers; and water. The skin-tightening compositions are useful for improving the appearance of skin, especially skin of the neck and face.

19 Claims, 1 Drawing Sheet

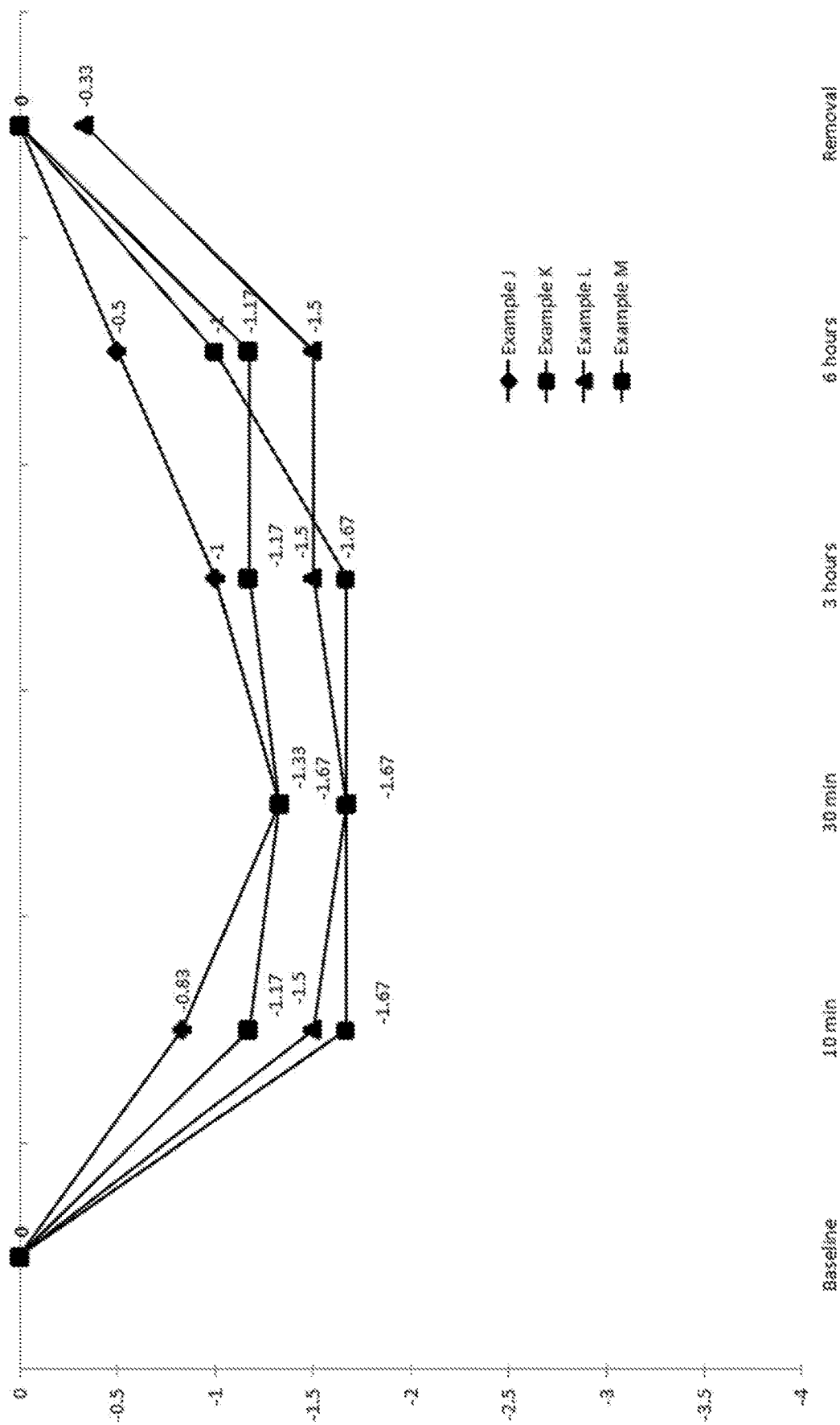

SKIN-TIGHTENING COMPOSITION

FIELD OF THE INVENTION

The instant disclosure relates to skin-tightening compositions and methods for using the same. The skin-tightening compositions provide a long-lasting skin-tightening effect and a mattifying finishing effect.

BACKGROUND OF THE INVENTION

Skin produces less collagen and elastin as it ages. For example, after the age of twenty, a person (human) produces about 1 percent less collagen in the skin each year. As a result, the skin becomes thinner and more fragile. Inevitably, wrinkles, crow's feet, age-spots, eye bags, and the like, begin to form.

Consumers often wish to improve the appearance of such age-related skin imperfections, preferably with instantaneous results. Many consumer products and procedures devoted to hiding and reducing wrinkles are available. Some products and procedures are simple and inexpensive, for example, applying make-up, particularly a primer or colored foundation, to cover the skin (and thereby cover and/or fill the wrinkles and provide a smoother look). Far more expensive and drastic procedures, such as surgical face lifts and Botox® injections, are also used to reduce the appearance of wrinkles. However, many consumers either cannot afford, or do not wish, to undergo such drastic skin-tightening procedures. There are a number of lotions and creams which are formulated to hydrate the skin and make it more supple, thereby reducing the appearance of wrinkles. Some of these products contain active ingredients, for example, niacinamide, that help repair and rejuvenate skin over time. Unfortunately, however, all of these products and procedures have drawbacks.

Attempts have been made to develop new categories of products to improve the appearance of skin without the drawbacks of existing products and procedures. One such family of products can be generally classified as "adhesive, contractile film formers." Film formers are chemical compositions that when applied to skin, leave a pliable, cohesive and continuous covering. A select group of film formers are also adhesive to the skin and contractile.

Compositions containing sodium silicate have been found to have dramatic, instant results. However, typical compositions containing sodium silicate quickly lose their skin tightening effect. For example, the films lose their elasticity and quickly begin to whiten, crack, and peel. Users may experience irritation and/or itchiness as certain films lose their elasticity and begin to crack and peel.

SUMMARY OF THE DISCLOSURE

The instant disclosure relates to skin-tightening compositions and methods for using the same. The skin-tightening compositions provide long-lasting skin-tightening effects as well as a mattifying effect. Without intending to be limited by any specific theory, the combination of long-lasting skin-tightening effects and mattifying effects is achieved by the synergistic interactions between the polyvalent silicate, hectorite, hydroxypropyl cellulose, and at least one of pullulan and galactoarabinan.

The instant disclosure is also directed to skin-tightening compositions that provide an instant cooling sensation, an instant skin-tightening effect, and/or instant mattifying effect. For example, the instant effects of cooling sensation, skin-tightening, and/or instant mattifying occur within 5 minutes, preferably within 2 minutes, preferably within 1 minute, preferably within 30 seconds of the application of the skin-tightening compositions to the skin. The effects of cooling sensation, skin-tightening, and/or instant mattifying may last at least 3 hours, at least 4 hours, at least 5 hours, at least 6 hours, at least 7 hours, or at least 8 hours.

The skin-tightening compositions are typically in the form of an oil-in-water emulsion and include:
- (a) at least 1 to about 15% of one or more polyvalent silicates;
- (b) about 1 to about 10 wt. % of one or more cellulose thickeners;
- (c) about 1 to about 10 wt. % of one or more clays selected from hectorite and organically modified hectorites;
- (d) about 0.1 to about 10 wt. % of one or more polysaccharide film forming agents;
- (e) about 1 to about 25 wt. % of one or more polyols;
- (f) about 0.1 to about 10 wt. % of one or more acrylate polymers; and
- (g) about 50 to about 90 wt. % of water,
  wherein the weight percentages are based on the total weight of the composition.

Non-limiting examples of polyvalent silicates include magnesium aluminum silicate, magnesium silicate, calcium silicate, aluminum silicate, polyvalent silicate clay, montmorillonite, bentonite, smectite, and a mixture thereof. For example, the polyvalent silicate may be an organically modified clay, such as those chosen from kaolinite, smectite, bentonite, and/or montmorillonite. In one instance, the polyvalent silicate comprises montmorillonite. In another instance, the polyvalent silicate comprises magnesium aluminum silicate.

Non-limiting examples of cellulose thickeners include hydroxyethylcellulose, hydroxymethylcellulose, hydroxypropylcellulose, methylcellulose, ethylhydroxyethylcellulose, carboxymethylcellulose, and a mixture thereof.

Non-limiting examples of organically modified hectorites include disteardimonium hectorite, stearalkonium hectorite, and a mixture thereof.

Non-limiting examples of polysaccharide film forming agents include those chosen from pullulan, galactoarabinan, xanthan gum, cellulose, cellulose derivatives, gellan gum, guars, carrageenan, pectin, and a mixture thereof. In some instances, the one or more polysaccharide film forming agents include at least one of pullulan and galactoarabinan.

Non-limiting examples of polyols include those having from 2 to 15 carbon atoms and at least two hydroxyl groups. For example, polyol(s) may be chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

Non-limiting examples of acrylate polymers include those chosen from acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof.

The skin-tightening composition may, in some instances, include one or more fatty compounds. For example, the one or more fatty compounds may be chosen from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In some instances, the one or more fatty compounds include one or more fatty acid triglycerides. In some instances, the one or more fatty acid triglycerides include caprylic/capric triglyceride.

The skin-tightening composition may also optionally comprise about 0.1 to about 20 wt. % of one or more emulsifiers. Non-limiting examples of nonionic emulsifiers include those selected from polyglyeryl-based emulsifiers, polyol esters, glycerol ethers, oxyethylenated and/or oxypropylenated ethers, ethylene glycol polymers, sorbitan esters, and a mixture thereof. Non-limiting examples of polyglyeryl-based emulsifiers include those chosen from polyglyceryl 10-stearate, polyglyceryl-3-caprate, polyglyceryl-3-diisostearate, polyglyceryl-3 methylglucose distearate, and a mixture thereof. The instant disclosure is also directed to methods for improving the appearance of skin by applying the skin-tightening compositions to the skin. The methods improve the appearance of the skin by treating or reducing the appearance of wrinkles, blemishes, dryness, roughness, dullness, age spots, sagging, eye bags, and/or puffy skin. Additionally and/or alternatively, the methods firm and/or tighten in the skin.

BRIEF DESCRIPTION OF THE DRAWING

The FIGURE a graph illustrating the reduction in eye bags over time provided by four skin-tightening compositions.

DETAILED DESCRIPTION OF THE DISCLOSURE

The instant disclosure relates to skin-tightening compositions and methods for using the same. The skin-tightening compositions provide long-lasting skin-tightening and mattifying effects. The skin-tightening compositions are particularly useful for improving the appearance of skin located around an individual's eyes by, e.g., treating and/or reducing eye-bags, crow's feet, and/or wrinkles located under the eyes. For example, the skin-tightening compositions provide a reduction in under eye bags that can last at least eight hours.

Typically, the skin-tightening compositions of the instant disclosure form an emulsion, such as a water-in-oil emulsion or an oil-in-water emulsion. For example, the skin-tightening compositions may be in the form of an oil-in-water emulsion and include:
  (a) at least 1 to about 15% of one or more polyvalent silicates;
  (b) about 1 to about 10 wt. % of one or more cellulose thickeners;
  (c) about 1 to about 10 wt. % of one or more clays selected from hectorite and organically modified hectorites;
  (d) about 0.1 to about 10 wt. % of one or more polysaccharide film forming agents;
  (e) about 1 to about 25 wt. % of one or more polyols;
  (f) about 0.1 to about 10 wt. % of one or more acrylate polymers; and
  (g) about 50 to about 90 wt. % of water;
    wherein the weight percentages are based on the total weight of the composition.

The skin-tightening compositions may be formulated to form a transparent film when applied to the skin. The skin-tightening compositions may form a transparent film when applied to the skin before drying of the skin-tightening compositions, after drying of the skin-tightening compositions, or both before and after drying of the skin-tightening compositions. In some instances the transparent film has a total transmittance of at least 70%, preferably at least 75%, preferably at least 80%, or more preferably at least 85%. In other instances, the transparent film has a total transmittance of about 70% and about 95%, about 75 to about 95%, or about 80% to about 95%. To determine transmittance, the skin-tightening composition can be applied onto a polyester film, such as those sold by the company Byk, using a film spreader to deposit a coat 50 um thick, which is left to dry for about 30 minutes at room temperature (25° C.). The transparency measurements are taken on the dry deposit obtained, using a Hazegard Plus machine from Bye Additive & Instruments.

Suitable components, such as those listed below, may be included in or excluded from the skin-tightening compositions, depending on the specific combination of other components, the form of the skin-tightening compositions, and/or the use of the formulation.

Polyvalent Silicates

The skin-tightening compositions typically include at least 1% to about 15%, by weight, of one or more polyvalent silicates. The amount of polyvalent silicates may range, for example, from about 1% to about 25%, about 1% to about 20%, about 1% to about 15%, about 1% to about 13%, about 1% to about 11%, about 1% to about 10%, about 1% to about 9%, about 1% to about 8%, about 1% to about 7%, about 1% to about 6%, from about 1.5% to about 25%, about 1.5% to about 20%, about 1.5% to about 15%, about 1.5% to about 13%, about 1.5% to about 11%, about 1.5% to about 10%, about 1.5% to about 9%, about 1.5% to about 8%, about 1.5% to about 7%, about 1.5% to about 6%, from about 2% to about 25%, about 2% to about 20%, about 2% to about 15%, about 2% to about 13%, about 2% to about 11%, about 2% to about 10%, about 2% to about 9%, about 2% to about 8%, about 2% to about 7%, about 2% to about 6%, from about 2.5% to about 25%, about 2.5% to about 20%, about 2.5% to about 15%, about 2.5% to about 13%, about 2.5% to about 11%, about 2.5% to about 10%, about 2.5% to about 9%, about 2.5% to about 8%, about 2.5% to about 7%, about 2.5% to about 6%, from about 3% to about 25%, about 3% to about 20%, about 3% to about 15%, about 3% to about 13%, about 3% to about 11%, about 3% to about 10%, about 3% to about 9%, about 3% to about 8%, about 3% to about 7%, about 3% to about 6%, from about 3.5% to about 25%, about 3.5% to about 20%, about 3.5% to about 15%, about 3.5% to about 13%, about 3.5% to about 11%, about 3.5% to about 10%, about 3.5% to about 9%, about 3.5% to about 8%, about 3.5% to about 7%, about 3.5% to about 6%, from about 4% to about 25%, about 4% to about 20%, about 4% to about 15%, about 4% to about 13%, about 4% to about 11%, about 4% to about 10%, about 4% to about 9%, about 4% to about 8%, about 4% to about 7%, about 4% to about 6%, by weight of the total weight of the skin-tightening composition.

The polyvalent silicates of the skin-tightening compositions may include at least one of or be chosen from magnesium aluminum silicate, magnesium silicate, calcium silicate, aluminum silicate, a polyvalent silicate clay, montmorillonite, bentonite, smectite, and a mixture thereof. The polyvalent silicates may be an organically modified clay and/or a polyvalent silicate compound derived from organically modified clay. For instance, the organically modified clay may be chosen from kaolinite, smectite, bentonite, and/or montmorillonite. Additional examples of polyvalent silicates that may, in some instances, be suitably included in the skin-tightening compositions are found in PCT patent publication no. WO 2013/109850 A2 and corresponding U.S. patent publication nos. 2013/189332 and 2013/195783, which are all incorporated herein in by reference in their entirety.

The polyvalent silicates may be an organically modified clay. For example, the polyvalent silicates may be an organically modified clay chosen from kaolinite, smectite, bentonite, and/or montmorillonite. In one embodiment, the polyvalent silicate comprises montmorillonite. In another embodiment, the polyvalent silicate comprises magnesium aluminum silicate.

Cellulose Thickener(s)

The skin-tightening compositions typically include one or more cellulose thickeners in an amount typically ranging from about 1% to about 10%, by weight based on the total weight of the skin-tightening compositions. In some instances, the skin-tightening compositions include cellulose thickening agents in an amount ranging from about 0.1% to about 15%, about 0.1% to about 10%, about 0.1% to about 8%, about 0.1% to about 6%, about 0.1% to about 5%, about 0.1% to about 4%, from about 0.5% to about 15%, about 0.5% to about 10%, about 0.5% to about 8%, about 0.5% to about 6% about 0.5% to about 5%, about 0.5% to about 4%, from about 1% to about 15%, about 1% to about 10%, about 1% to about 8%, or about 1% to about 6% about 1% to about 5%, about 1% to about 4%, from about 1.5% to about 15%, about 1.5% to about 10%, about 1.5% to about 8%, or about 1.5% to about 6% about 1.5% to about 5%, about 1.5% to about 4%, by weight of the total composition, including ranges and sub-ranges therebetween.

The cellulose thickeners may comprise at least one of or be chosen from hydroxyethylcellulose, hydroxymethylcellulose, hydroxypropylcellulose, methylcellulose, ethylhydroxyethylcellulose, carboxymethylcellulose, and a mixture thereof. Additional cellulose thickeners that may be included in the skin-tightening composition include, e.g., cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, alkyl-substituted celluloses and mixtures thereof. Among the alkyl hydroxyalkyl cellulose ethers, cetyl hydroxyethylcellulose, which is the ether of cetyl alcohol and hydroxyethylcellulose, may be useful, in some cases.

Clay(s)

The skin-tightening compositions typically include one or more clays selected from hectorite and organically modified hectorites in an amount that typically ranges from about 1% to about 10%, by weight. In some instances, the amount of the one or more clays range from about 0.1% to about 15%, about 0.1% to about 10%, about 0.1% to about 8%, about 0.1% to about 6%, about 0.1% to about 5%, about 0.1% to about 4%, from about 0.5% to about 15%, about 0.5% to about 10%, about 0.5% to about 8%, about 0.5% to about 6% about 0.5% to about 5%, about 0.5% to about 4%, from about 1% to about 15%, about 1% to about 10%, about 1% to about 8%, or about 1% to about 6% about 1% to about 5%, about 1% to about 4%, from about 1.5% to about 15%, about 1.5% to about 10%, about 1.5% to about 8%, or about 1.5% to about 6% about 1.5% to about 5%, about 1.5% to about 4%, by weight of the total composition, including ranges and sub-ranges therebetween.

The one or more clays of the skin-tightening compositions may be selected from hectorite and organically modified hectorites. These clays can be of natural or synthetic origin. For example, the clay may be a synthetic hectorites (also known as laponites), such as the products sold by Rockwood Additives Limited under the names LAPONITE XLS, LAPONITE XLG, LAPONITE RD, LAPONITE RDS and LAPONITE XL21 (these products are sodium magnesium silicates and in particular sodium lithium magnesium silicates).

The clays used in the skin-tightening composition may be modified hectorite. In some instances, the hectorite clay is an organophilic modified hectorite. Additionally and/or alternatively, the clays may be modified with a chemical compound chosen from quaternary amines, tertiary amines, amine acetates, imidazolines, amine soaps, fatty sulfates, alkylarylsulfonates and amine oxides, and mixtures thereof. Mention may be made of hectorites modified with a quaternary amine, more specifically with a C10 to C22 fatty acid ammonium halide, such as a chloride, such as hectorite modified with distearyldimethylammonium chloride (CTFA name: Disteardimonium hectorite), for instance the product sold under the name BENTONE 38V, BENTONE 38V CG or BENTONE EW CE by the company Elementis, or stearalkonium hectorites, such as BENTONE 27 V. The clay may, in some instances, be disteardimonium hectorite or distearyldimethylammonium chloride (CTFA name: Disteardimonium hectorite).

In one embodiment, the one or more clays comprise an organically modified hectorite selected from disteardimonium hectorite, stearalkonium hectorite, and a mixture thereof.

Polysaccharide Film Forming Agent(s)

The skin-tightening composition typically includes at least one polysaccharide film forming agent in an amount that typically ranges from about 0.1% to about 10%, by weight based on the total weight of the skin-tightening composition. For example, the total amount of polysaccharide film forming agent may be from about 0.1% to about 15%, 0.1% to about 10%, about 0.1% to about 8%, about 0.1% to about 6%, about 0.1% to about 5%, about 0.1% to about 4%, from about 0.5% to about 15%, about 0.5% to about 10%, about 0.5% to about 8%, about 0.5% to about 6%, from about 0.5% to about 5% about 0.5% to about 4%, from about 0.8% to about 15%, about 0.8% to about 10%, about 0.8% to about 8%, about 0.8% to about 6%, from about 0.8% to about 5%, about 0.8% to about 4%, including ranges and sub-ranges therebetween, by weight based on the total weight of the skin-tightening composition. In one instance, the total amount of polysaccharide film forming agent in the skin-tightening composition is an amount from 0.5%, 0.6%, 0.7%, 0.8%, 0.9%, or 1.0% to 5%, 6%, 7%, 8%, 9%, or 10%, by weight based on the total weight of the skin-tightening composition.

The polysaccharide film forming agents enable the skin-tightening composition to form a pliable, cohesive, and continuous film that covers the user's skin when applied. The polysaccharide film forming agents may also facilitate gelling, thickening, and emulsion stabilization. The polysaccharide film forming agent may be chosen from gellan gum, xanthan gum, agar, carrageenan, locust bean gum, acacia senegal gum, guar gum, and konjac mannan gum. Additionally and/or alternatively, the polysaccharide film forming agent may be chosen from gellan gum, xanthan gum, agar, carrageenan, locust bean gum, acacia senegal gum, guar gum, welan, karaya gum, okra gum, aloe gum, gum targacanth, gum ghatti, quinceseed gum, psyllium, starch arabinogalactan, and konjac mannan gum as well as any combination thereof. Additional description of polysaccharide film forming agent may be found in U.S. patent publication no. 20140356302, which is incorporated herein by reference in its entirety.

Gellan gum is a tetrasaccharide having two residues of D-glucose and one of each residues of L-rhamnose and D-glucuronic acid. Xanthan Gum is a pentasaccharide comprising glucose, mannose, and glucuronic acid in the molar ratio 2.0:2.0:1.0. Agar is a polysaccharide comprising agrose units. Locust Bean Gum and Guar Gum contain the polysaccharide Galactomannan which is a high-molecular-weight hydrocolloidal polysaccharides comprising galactose and mannose units. A cacia Senegal Gum, a grade of Gum Arabic, is a biopolymer comprising arabinose and galactose monosaccharides. Konjac Mannan Gum contains the polysaccharide Glucomannan, a straight-chain polymer with a small amount of branching comprising .beta.-(1.fwdarw.4)-linked D-mannose and D-glucose in a ratio of 1.6:1.

Carrageenan is a linear sulfated polysaccharide with a high-molecular-weight made up of repeating galactose units and 3,6 anhydrogalactose units. Carrageenan is a linear sulfated polyshardide with a high-molecular-weight made up of repeating galactose units and 3,6 anhydrogalactose units. Carrageenan may be used to additionally increase the gelling, thickening, and/or emulsion stabilizing properties of the skin-tightening composition.

In one embodiment, the skin-tightening composition includes polysaccharide film forming agents selected from pullulan, galactoarabinan, xanthan gum, cellulose, cellulose derivatives, gellan gum, guars, carrageenan, pectin, and a mixture thereof. In another embodiment, the one or more polysaccharide film forming agents comprise at least one of pullulan and galactoarabinan.

Polyol(s)

The skin-tightening compositions typically include one or more polyols. The one or more polyols may be chosen from polyols having from 2 to 15 carbon atoms and at least two hydroxyl groups. Non-limiting examples of polyols that may be used in the skin-tightening composition include and/or may be chosen from alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, in some instances, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In one embodiment, the one or more polyols include or are chosen from ethylene glycol, propylene glycol, butylene glycol, hexylene glycol, pentylene glycol, 1,3-propanediol, diethylene glycol, dipropylene glycol, caprylyl glycol, glycerin, and a mixture thereof. In another embodiment, the skin-tightening composition includes or is chosen from caprylyl glycol, glycerin, and a mixture thereof. In yet a further embodiment, the one or more polyols include glycerin.

The amount of polyols in the skin-tightening composition may vary, but generally ranges from about 1% to about 35%, by weight based on the total weight of the skin-tightening composition. For example, the total amount of polyols may be from about 0.1% to about 35%, about 0.1% to about 30%, about 0.1% to about 25%, about 0.1% to about 20%, about 0.1% to about 15%, about 0.1% to about 10%, about 0.1% to about 8%, about 0.1% to about 7%, from about 1% to about 35%, about 1% to about 30%, about 1% to about 25%, about 1% to about 20%, about 1% to about 15%, about 1% to about 10%, about 1% to about 8%, about 1% to 7%, from about 2% to about 35%, about 2% to about 30%, about 2% to about 25%, about 2% to about 20%, about 2% to about 15%, about 2% to about 10%, about 2% to about 8%, or about 2% to about 7%, from about 3% to about 35%, about 3% to about 30%, 3% to about 25%, about 3% to about 20%, about 3% to about 15%, about 3% to about 10%, about 3% to about 8%, or about 3% to about 7%, from about 4% to about 35%, about 4% to about 30%, about 4% to about 25%, about 4% to about 20%, about 4% to about 15%, about 4% to about 10%, about 4% to about 8%, or about 4% to about 7%, including ranges and sub-ranges therebetween, by weight based on the total weight of the skin-tightening composition.

Acrylate Polymer(s)

The skin-tightening compositions include an amount of one or more acrylate polymers typically ranging from about 0.1 to about 10 wt. % of one or more. For example, the amount of the acrylate polymers can vary but may be from about 0.01% to about 10%, by weight based on the total weight of the skin-tightening composition. In some instances, the amount of acrylate polymers is from about 0.01% to about 8%, about 0.01% to about 5%, about 0.01% to about 3%, about 0.1% to about 10%, about 0.1% to about 8%, about 0.1% to about 6%, about 0.1% to about 5%, or about 0.1% to about 3%, by weight based on the total weight of the skin-tightening composition.

The acrylate polymer(s) may be an acrylate copolymer or acrylate monomer. For example, the one or more acrylate polymers may be crosslinked polyacrylate polymers that are useful as thickeners or gelling agents, including both cationic and nonionic polymers. Examples of crosslinked nonionic polyacrylate polymers and crosslinked cationic polyacrylate polymers that may be useful in some instances are those described in U.S. Pat. Nos. 5,100,660, 4,849,484, 4,835,206, 4,628,078 U.S. Pat. No. 4,599,379 and EP 228, 868, which are all incorporated herein by reference in their entirety for all purposes.

Non-limiting examples of thickening agents include polyacrylate crosspolymer, cationic acrylate copolymer, hydroxypropyl cellulose, polyquaterniums, polyvinylpyrrolidone homopolymer/copolymer, 12-hydroxystearic acid, sugar esters, polyglycery esters, and a mixture thereof. Particular types of thickening agents that may be mentioned include the following:

Polyacrylate Homopolymer or Co-Polymer

Polyacrylate homopolymer or co-polymer can be linear or crosslinked. Non-limiting examples include acrylates/C10-30 alkyl acrylate crosspolymers, copolymers of acrylic acid and alkyl C5-C10 acrylate, copolymers of acrylic acid and maleic anhydride, carbomers, polyacrylate crosspolymer-6, and mixtures thereof. Commercially available polymers of the polyacrylate type include those sold under the trade names CARBOPOL, ACRYSOL ICS-1, POLYGEL, SOKALAN, CARBOPOL 1623, CARBOPOL 695, ULTREZ 10, and POLYGEL DB.

In some instances, the skin-tightening compositions include one or more polyacrylate crosspolymers, such as polyacrylate crosspolymer-6. In further instances, the skin-tight compositions include acrylamidopropyltrimonium chloride/acrylates copolymer, which is a copolymer of one or more of the monomers formed from the amide of acrylic acid, methacrylic acid and aminopropyltrimethyl-ammonium chloride and one or more monomers of acrylic acid, methacrylic acid or one of their esters.

Carboxylic Acid Based Homopolymer or Co-Polymer

The acrylate polymer(s) may, in some instances, be formed from carboxylic acids or polymers formed therefrom. Carboxylic acid based homopolymer or co-polymer can be linear or crosslinked. These polymers contain one or more monomers derived from acrylic acid, substituted acrylic acids, and salts and esters of these acrylic acids and the substituted acrylic acids. Examples of commercially available carboxylic acid polymers include carbomers, which are homopolymers of acrylic acid crosslinked with allyl ethers of sucrose or pentaerytritol. Carbomers are available as the CARBOPOL 900 series from B.F. Goodrich (e.g., Carbopol® 954). In addition, other suitable carboxylic acid polymeric agents may include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

In one embodiment, the one or more acrylate polymers include those chosen from acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof. In another embodiment, the acrylate polymers include at least sodium acrylates copolymer.

Fatty Compound(s)

The skin-tightening composition may include one or more fatty compounds, which may be liquid or solid at room temperature and at atmospheric pressure (25° C., 1 atm). Fatty compounds are typically organic compounds that are not soluble in water at normal temperature (25° C.) and at atmospheric pressure (750 mmHg) (solubility below 10%). In some instances, the solubility in water may be below 5%, below 1%, or below 0.1%.

The total amount of fatty compounds in the skin-tightening compositions may vary from, e.g., about 0.1% to about 25%, by weight based on the total weight of the skin-tightening composition. For example, the total amount of fatty compounds may be from about 0.1% to about 25%, about 0.1% to about 20%, about 0.1% to about 15%, about 0.1% to about 10%, about 0.1% to about 8%, about 0.1% to about 6%, about 0.1% to about 5%, about 0.1% to about 4%, from about 0.5% to about 25% about 0.5% to about 20%, about 0.5% to about 15%, about 0.5% to about 10%, about 0.5% to about 8%, about 0.5% to about 6% about 0.5% to about 5%, about 0.5% to about 4%, from about 1% to about 25%, about 1% to about 20%, about 1% to about 15%, about 1% to about 10%, about 1% to about 8%, or about 1% to about 6% about 1% to about 5%, about 1% to about 4%, by weight of the total composition, including ranges and subranges therebetween.

Non-limiting examples of fatty compounds of the skin-tightening composition include or may be chosen from oils, mineral oil, fatty alcohols, fatty acids, fatty alcohol derivatives, fatty acid derivatives (e.g., alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), glyceryl esters (glycerol esters), alkyl ethers of fatty alcohols, fatty acid esters of alkyl ethers of fatty alcohols, fatty acid esters of alkoxylated fatty alcohols, fatty acid esters of alkyl ethers of alkoxylated fatty alcohols, esters of fatty alcohols, hydroxy-substituted fatty acids, waxes, triglyceride compounds, lanolin, and a mixture thereof. In some instances, the one or more fatty compound may comprise or be chosen from fatty alcohols, fatty acids, esters of fatty acids, and/or esters of fatty alcohols (e.g., cetyl palmitate, cetyl stearate, myristyl myristate, myristyl stearate, cetyl myristate, and stearyl stearate (a mixture of which is referred to as "cetyl esters")). Additionally or alternatively, the one or more fatty compounds may include or be chosen from hydrocarbons, fatty alcohols, fatty alcohol derivatives, fatty acids, fatty acid derivatives, fatty esters, fatty ethers, oils, waxes, etc. In one instance, the one or more fatty compounds is a hydrocarbon that is linear, branched, and/or cyclical, such as cyclic $C_6$-$C_{16}$ alkanes, hexane, undecane, dodecane, tridecane, and isoparaffins, for instance isohexadecane, isododecane and isodecane. Additionally, the linear or branched hydrocarbons may be composed only of carbon and hydrogen atoms of mineral, plant, animal or synthetic origin with more than 16 carbon atoms, such as volatile or non-volatile liquid paraffins, petroleum jelly, liquid petroleum jelly, polydecenes, hydrogenated polyisobutene, and squalane.

Fatty Alcohols

The one or more fatty compounds may be glycerolated and/or oxyalkylenated, include from 8 to 30 carbon atoms, and/or be saturated or unsaturated. The fatty alcohols useful herein include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, cetyl alcohol, stearyl alcohol, isostearyl alcohol, oleyl alcohol, isotridecyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

Fatty Esters

The fatty compounds of the skin-tightening composition may be liquid or solid fatty esters at 25° C., 1 atm. The fatty esters may include esters from a $C_6$-$C_{32}$ fatty acid and/or a $C_6$-$C_{32}$ fatty alcohol. For example, the fatty compounds may include or be chosen from fatty acid monoesters and diesters, polyol esters, polyglycerol esters, polyglycerol polyricinoleate, polyglycerol poly-12-hydroxystearate, polyglycerol dimerate isostearate, ethylhexanoate, polyglycerol esters, and a mixture thereof. These esters may be esters of saturated or unsaturated, linear or branched $C_1$-$C_{26}$ aliphatic mono or polyacids and of saturated or unsaturated, linear or branched $C_1$-$C_{25}$ aliphatic mono or polyalcohols, the total number of carbon atoms in the esters being greater than or equal to 10. In one instance, the fatty compounds comprise one or more fatty acid monoesters. For the esters of monoalcohols, at least one of the alcohol or the acid from which the esters result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate and isostearyl neopentanoate.

In some instances, the fatty esters are cetyl esters, such as esters of saturated fatty acids and fatty alcohols. For example, the fatty esters may include or be chosen from cetyl palmitate, cetyl stearate, myristyl myristate, myristyl stearate, cetyl myristate, stearyl stearate, cetearyl ethylhexanoate, and mixtures thereof. In one instance, the fatty esters may be one or more of or chosen from isopropyl isostearate, n-propyl myristate, isopropyl myristate, hexyl laurate, hexadecyl isostearate, hexydecyl laurate, hexyldecyl octanoate, n-propyl palmitate, isopropyl palmitate, and mixtures thereof. In another instance, the fatty esters include or may be chosen from diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palm itate, 2-ethylhexyl palm itate, 2-hexyldecyl palm itate, 2-heptylundecyl palm itate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, diisostearyl malate, dicaprylyl carbonate, cetearyl ethylhexanoate, and mixtures thereof. In yet a further instance, the skin-tightening composition includes one or more of or may have fatty compounds chosen from cetearyl alcohol, cetearyl ethylhexanoate, isopropyl myristate, and mixtures thereof.

Non-limiting examples of solid fatty acid esters and/or fatty acid esters that may be mentioned include solid esters obtained from $C_9$-$C_{26}$ fatty acids and from $C_9$-$C_{25}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

Non-limiting examples of liquid fatty acid include triglyceride oils of plant or synthetic origin, such as liquid fatty acid triglycerides containing 6 to 30 carbon atoms, for instance heptanoic or octanoic acid triglycerides, or alternatively, e.g., sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, shea butter oil, and mixtures thereof.

In one instance, the one or more fatty compounds include at least one of or are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof. In another instance, the one or more fatty compounds include one or more fatty acid triglycerides, such as caprylic/capric triglyceride.

Fatty Alcohol Derivatives

The skin-tightening compositions may, in some instances, include fatty alcohol derivatives such as alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof. Liquid fatty ethers may be chosen from liquid dialkyl ethers such as dicaprylyl ether. The non-liquid fatty ethers may also be chosen from dialkyl ethers and in particular dicetyl ether and distearyl ether, alone or as a mixture.

Esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate; diisopropyl sebacate; diisopropyl adipate; di-n-propyl adipate; triisopropyl citrate; glyceryl trilactate; glyceryl trioctanoate; neopentyl glycol diheptanoate; and diethylene glycol diisononanoate.

Fatty Acid Derivatives

The skin-tightening compositions may, in some instances, include fatty acid derivatives. The fatty acid derivatives are defined herein to include fatty acid esters of the fatty alcohols as defined above, fatty acid esters of the fatty alcohol derivatives as discussed above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof.

Emulsifier(s)

The skin-tightening compositions may include one or more emulsifiers. The emulsifiers may be amphoteric, anionic, cationic or nonionic emulsifier, used alone or as a mixture, and optionally with a co-emulsifier. The emulsifiers are chosen in an appropriate manner according to the emulsion to be obtained.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM 90™ by the company Goldschmidt.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The one or more emulsifiers may be oxyalkylenated organosiloxane emulsifiers. The oxyalkylenated organosiloxane emulsifiers may be fully or partially crosslinked and/or be elastomeric or non-elastomeric. They are sometimes referred to as "emulsifying elastomers" because of they have both elastomeric and emulsifying properties. In some instances, the one or more emulsifiers include an oganosiloxane emulsifier, including crosslinked organosiloxane emulsifiers. For example, the skin-tightening compositions may comprise one or more crosslinked organosiloxane emulsifier including or chosen from dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer, and mixtures thereof.

In another instance, the skin-tightening compositions include one or more linear organosiloxane emulsifier chosen from cyclotetrasiloxane (and) cyclopentasiloxane (and) PEG/PPG-18 dimethicone; cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone; and mixtures thereof.

The skin-tightening composition may, in some instances, include an oxyalkylenated organosiloxane emulsifier. The oxyalkylenated organosiloxane emulsifier may have a structure in accordance with the following general formula:

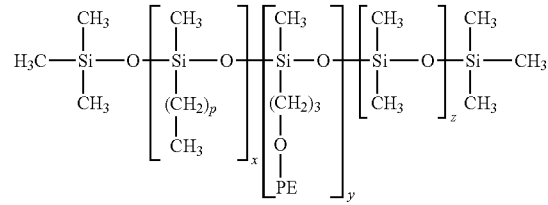

wherein p is 0-40 (the range including all numbers between and subranges such as 2, 3, 4, 13, 14, 15, 16, 17, 18, etc.), and PE is (—C2H4O)a-(-C3H6O)b-H wherein a is 0-25, b is 0-25 with the proviso that both a and b cannot be 0 simultaneously, x, y, and z are each independently ranging from 0 to 1 million with the proviso that x and y cannot be 0 simultaneously. In some instances, x, y, z, a, and b are such that the molecular weight of the polymer ranges from about 5,000 to about 500,000, from about 10,000 to 100,000, or is about 50,000, and the polymer is generically referred to as dimethicone copolyol. In additional instances, p is such that the long chain alkyl is cetyl or lauryl, and the compound is called, generically, cetyl dimethicone copolyol or lauryl dimethicone copolyol respectively. In some cases, the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

The oxyalkylenated organosiloxane emulsifier may alternatively have a structure in accordance with the following general formula:

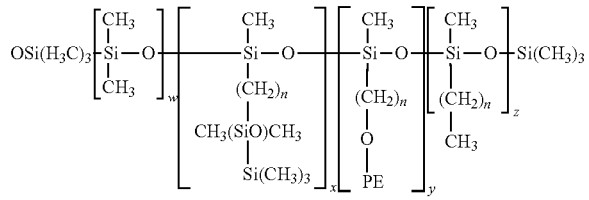

wherein each n is independently 0-100 with the proviso that there must be at least one PE radical. In some instances, where each n independently ranges from about 2 to 30, and PE (—C2H4O)a-(-C3H6O)b-H wherein a is 0-25, b is 0-25 with the proviso that both a and b cannot simultaneously be 0; and wherein w, x, y, and z are each independently 0 to 1,000,000 with the proviso that there is at least one PE. In some embodiments, the organosiloxane emulsifier is lauryl PEG-9 Polydimethylsiloxyethyl Dimethicone. Oxyalkylenated organosiloxane emulsifiers disclosed in U.S. Pat. No. 9,095,543 may be useful in the skin-tightening compositions. U.S. Pat. No. 9,095,543 is incorporated herein by reference in its entirety for all purposes.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

The one or more emulsifiers may, in some instances, be polyoxyalkylenated silicone elastomers, such as, e.g., those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer. The polyglycerolated silicone elastomers may include or be chosen from dimethicone/polyglycerin-3 crosspolymer dispersed in dimethicone; or lauryl dimethicone/polyglycerin-3 crosspolymer dispersed in a variety of solvents such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

The emulsifiers may, in some instances, be nonionic a surfactant, such as one chosen from: alkanolamides; alkyl polyglucosides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Additional nonionic surfactants that may, in some instances, be suitable include, e.g., alcohols, alpha-diols, alkylphenols and esters of fatty acids, being ethoxylated, propoxylated, or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C6-C24) alkylpolyglycosides; N—($C_6$-$C_{24}$)alkylglucamine derivatives, amine oxides such as (C10-C14)alkylamine oxides or N—($C_{10}$-$C_{14}$)acylaminopropylmorpholine oxides; and mixtures thereof.

In some cases, the nonionic surfactant may be chosen from esters of polyols with fatty acids with a saturated or unsaturated chain containing for example from 8 to 24 carbon atoms, and alkoxylated derivatives thereof; polyethylene glycol esters of a $C_8$-$C_{24}$; sorbitol esters of a $C_8$-$C_{24}$; sugar (sucrose, glucose, alkylglycose) esters of a $C_8$-$C_{24}$, preferably $C_{12}$-$C_{22}$, fatty acid or acids and alkoxylated derivatives thereof; ethers of sugar and a $C_8$-$C_{24}$, preferably $C_{12}$-$C_{22}$, fatty alcohol or alcohols; and mixtures thereof. In one instance, the nonionic surfactant is an ethoxylated fatty ester chosen from adducts of ethylene oxide with esters of lauric acid, palmitic acid, stearic acid or behenic acid, and mixtures thereof. Examples of ethoxylated fatty esters that may be suitable include those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

The nonionic surfactant may be chosen from glyceryl esters of fatty acids, glyceryl stearate (glyceryl mono-, di- and/or tristearate) (CTFA name: glyceryl stearate); glyceryl ricinoleate; glyceryl esters of $C_8$-$C_{24}$ alkoxylated fatty acids, such as polyethoxylated glyceryl stearate (glyceryl mono-, di- and/or tristearate), and PEG-20 glyceryl stearate; and mixtures thereof.

In some instances, the skin-tightening composition composition may include an emulsifier such as dimers surfactants named "gemini surfactants," which may have two surfactant moieties identical or different, and constituted by a hydrophilic head group and a lipophilic group linked to each other through the head groups by way of a spacer. For example, the one or more emulsifiers may include or be chosen from those sold by Sasol company under the name CERALUTIOM, for example, CERALUTION H: Behenyl Alcohol, Glyceryl Stearate, Glyceryl Stearate Citrate et Sodium Dicocoyl ethylenediamine PEG-15 Sulfate, CERALUTION F: Sodium Lauroyl Lactylate et Sodium Dicocoyl ethylenediamine PEG-15 Sulfate, CERALUTION C: Aqua, Capric/Caprylic triglyceride, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben. The emulsifier of the skin-tightening composition may include sodium lauroyl lactylate, optionally, with one or more additional emulsifiers, such as a nonionic emulsifier or an anionic emulsifier.

In one embodiment, the one or more emulsifiers are selected from polyglyeryl-based emulsifiers, polyol esters, glycerol ethers, oxyethylenated and/or oxypropylenated ethers, ethylene glycol polymers, sorbitan esters, and a mixture thereof. The one or more polyglyeryl-based emulsifiers may be selected from polyglyceryl 10-stearate, polyglyceryl-3-caprate, polyglyceryl-3-diisostearate, polyglyceryl-3 methylglucose distearate, and a mixture thereof. In one embodiment, the emulsifiers include at least one or optionally at least two of polyglyceryl-3 methylglucose distearate, steareth-20, and lecithin.

The total amount of emulsifiers in the skin-tightening compositions may vary from, e.g., about 0.001% to about 25%, by weight based on the total weight of the composition. For example, the total amount of emulsifiers may be from about 0.1% to about 25%, about 0.1% to about 20%, from about 0.1% to about 15%, about 0.1% to about 10%, about 0.1% to about 8%, about 0.1% to about 6%, from about 0.5% to about 25%, about 0.5% to about 20%, about 0.5% to about 15%, about 0.5% to about 10%, about 0.5% to about 8%, about 0.5% to about 6%, from about 0.8% to about 25%, about 0.8% to about 20%, about 0.8% to about 15%, about 0.8% to about 10%, about 0.8% to about 8%, about 0.8% to about 6%, from about 1% to about 25%, about 1% to about 20%, about 1% to about 15%, about 1% to about 10%, about 1% to about 8%, or about 1% to about 6% including ranges and sub-ranges therebetween, by weight based on the total weight of the skin-tightening composition. In one instance, the total amount of emulsifiers in the skin-tightening composition is an amount from 0.5%, 0.6%, 0.7%, 0.8%, 0.9%, or 1.0% to 5%, 6%, 7%, 8%, 9%, or 10%, by weight based on the total weight of the skin-tightening composition.

The skin-tightening composition may be formulated to have a lower amount of emulsifier(s) than typical commercial products. For example, the skin-tightening composition may have a total amount of emulsifiers ranging from about 0.1% to about 6%, about 0.1% to about 5%, about 0.1% to about 4%, about 0.1% to about 3%, from about 0.5% to about 5% about 0.5% to about 4%, about 0.5% to about 3%, from about 0.8% to about 5%, about 0.8% to about 4%, about 0.8% to about 3%, from about 1% to about 6%, about 1% to about 5%, about 1% to about 4%, about 1% to about 3%, including ranges and sub-ranges therebetween, by weight based on the total weight of the composition.

Thickening Agent(s)

In addition to the cellulose thickeners and the acrylate polymers, the skin-tightening composition may comprise further thickening agents. The amount of these additional thickening agents may depend on the other components in skin-tightening composition and desired viscosity for the skin-tightening composition. For example, the skin-tightening composition may include an amount of these thickening agents such that the viscosity of the skin-tightening composition is about 1,000 cP to about 1,000,000 cP, about 5,000 cP to about 500,000 cP, about 10,000 to about 250,000 cP, or about 15,000 cP to about 100,000 cP at a temperature of 25° C. using a Brookfield rheometer. In some instances, the Brookfield rheometer is used with a spindle number 5 at 20 revolutions per minute.

The skin-tightening composition may include an amount of thickening agents, in addition to the amount of cellulose thickeners and acrylate polymers, that ranges from about 0.1% to about 20%, about 0.1% to about 10%, about 0.1% to about 9%, about 0.2% to about 9%, about 0.3% to about 9%, about 0.4% to about 8%, about 0.5% to about 5%, about 0.8% to about 20%, about 0.8% to about 5%, or about 0.8% to about 3%, including ranges and sub-ranges therebetween, based on the total weight of the skin-tightening composition. Further, the skin-tightening composition may include an amount of thickening agents, other than the cellulose thickeners and acrylate polymers, that range from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %, including ranges and sub-ranges therebetween, based on the total weight of the skin-tightening composition.

The thickening agent(s), other than the cellulose thickeners and acrylate polymers discussed herein that may be included in the skin-tightening composition include, e.g., xanthan gum, guar gum, biosaccharide gum, acacia Seneca gum, sclerotium gum, agarose, pechtin, gellan gum, hyaluronic acid. Additionally, these thickening agents may include polymeric thickeners chosen from ammonium polyacryloyldimethyl taurate, ammonium acryloyldimethyltaurate/VP copolymer, polyacrylamide, and carbomer. In one instance, the skin-tightening composition includes at least one of or is chosen from ammonium polyacryloyldimethyl taurate from ammonium polyacryloyldimethyl taurate, xanthan gum, carbomer, and a mixture thereof.

Many thickening agents are water-soluble and increase the viscosity of water or form an aqueous gel when the skin-tightening composition is aqueous. The aqueous solution may be heated and cooled, or neutralized, for forming the gel, if necessary. The thickener(s) may be dispersed/dissolved in an aqueous solvent that is soluble in water, e.g., ethyl alcohol when it is dispersed/dissolved in water. Non-limiting examples of various types of thicken agents, which may be included in addition to the cellulose thickeners and acrylate polymers discussed herein, include:

Carboxylic Acid Polymers

In some instances, carboxylic acid polymer may be used in the skin-tightening composition. Carboxylic acid polymer are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of carboxylic acid polymers that may, in some instances, be included in the skin-tightening compositions include one or more of or may be chosen from carbomers, which are homopolymers of acrylic acid crosslinked with allyl ethers of sucrose or pentaerytritol.

Commercially available carbomers include Carbopol®, 900 series from B.F. Goodrich (e.g., Carbopol® 954). Other carboxylic acid polymeric agents worth mentioning include Ultrez® 10 (B.F. Goodrich) and copolymers formed from monomers of acrylic acid, methacrylic acid, or one of their short chain (i.e., C1-4 alcohol) esters, wherein the crosslinking agent is an allyl ether of sucrose or pentaerytritol.

Polyacrylamide Polymers

The skin-tightening compositions can optionally contain polyacrylamide polymers, such as nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. Other polyacrylamide polymers that may be included in the skin-tightening composition include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. In one instance, the skin-tightening composition includes thickening and texturizing gels of the type as exemplified by the product range called Lubrajel® from United Guardian. These gels have moisturizing, viscosifying, stabilizing properties.

Gums

Other thickening agents that may be used, in some instances, include gums, which may be primarily or entirely derived from natural sources. Non-limiting examples of gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

The water-soluble thickeners may be water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example, starch derived from corn, potato, wheat, rice, sweet potato and tapioca, a-starch, soluble starch), fermentation polysaccharide (for example, xanthan gum, pullulan, carciran, dextran), acidic hetero-polysaccharide derived from callus of plants belonging to Polyantes sp. (for example, tuberous polysaccharide), proteins (for example, sodium casein, gelatin, albumin), chondroitin sulfate, and hyaluronic acid.

The skin-tightening composition may include water-soluble synthetic polymers including, e.g., polyvinyl alcohol, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Pigments, Colorants, and Soft Focus Powder

The skin-tightening compositions may optionally include one or more pigments, colorants, and/or soft focus powders. Pigments, colorants, and soft focus powders may be included so that the skin-tightening composition is not clear and/or translucent. The amount of pigments, colorants, and/or soft focus powders included in the skin-tightening composition may vary depending on the product and the desired appearance. Provided below are lists of pigments, colorants, and/or soft focus powders that may be suitably included in some instances of the skin-tightening composition:

Pigments

Non-limiting examples include titanium dioxide, zirconium oxide, cerium oxide, zinc oxide, iron oxide, tin oxide, MICA, alumina, aluminum hydroxide, chromium oxide, manganese violet, ultramarine blue, chromium hydrate, ferric blue, aluminum powder, copper powder, silver powder, gold powder, barium sulfate, carbon black, and mixtures thereof.

The total amount of pigments, if present, may vary but is typically about 0.01% to about 10%, by weight based on the total weigh of the skin-tightening composition. The total amount of inorganic pigments may be about 0.01% to about 8%, about 0.01% to about 5%, about 0.01% to about 4%, about 0.1% to about 10%, about 0.1% to about 8%, about 0.1% to about 5%, or about 0.1% to about 4%, by weight based on the total weight of the skin-tightening composition.

Colorants

Non-limiting examples include D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminium lakes.

The total amount of colorants, if present, may vary but is typically about 0.01% to about 10%, by weight based on the total weigh of the skin-tightening composition. The total amount of coloarants may be about 0.01% to about 8%, about 0.01% to about 5%, about 0.01% to about 4%, about 0.1% to about 10%, about 0.1% to about 8%, about 0.1% to about 5%, or about 0.1% to about 4%, by weight based on the total weight of the skin-tightening composition.

Soft Focus Powder

The skin-tightening compositions may optionally include a soft focus powder. Soft focus powders are materials providing a blurring effect, typically due to their light-scattering properties on the skin. Such powders typically have high diffuse reflectance, low specular reflectance, and high diffuse transmittance. Soft focus powders give the skin a smoother appearance, for example, by reducing the difference in luminosity between the valley and the edges of wrinkles and imperfections.

Non-limiting examples of soft focus powders include powders of natural or synthetic origin such as mica, titanated mica, alumina, titanium dioxide, serecite, composite talc/titanium dioxide/alumina/silica powders, polyamide, poly(methyl (meth)acrylate), polyethylene powder, polymethylsilsesquioxane powder, sodium acrylates crosspolymer-2 and a mixture thereof. Additional non-limiting examples include calcium aluminum borosilicate (LUXSIL), PMMA (Microsphere M-100), polyethylene (POLYETHYLENE CI 2080), methyl methacrylate crosspolymer (COVABEADS LH85), nylon-12 (ORGASOL 2002), or ethylene/acrylic acid copolymer (FLOBEADS EA209). In some instances, the skin-tightening compositions include at least one soft focus powder selected from the group consisting of silica which may or may not be coated, fumed silica, silica silylate, composite talc/titanium dioxide/alumina/silica powders, polyamide (nylon), poly(methyl (meth)acrylate), polyethylene powder, polymethylsilsesquioxane powder, waxes, such as copernicia cerifera (carnauba) wax, dimethicone/vinyl dimethicone crosspolymer, nylon-12, cellulose, polylactic acid, boron nitride, and a mixture thereof. The copernicia cerifera (carnauba) wax can be provided as a dispersion non water and alcohol. The dimethicone/vinyl dimethicone crosspolymer can be provided as silicone dispersion (INCI: Dimethicone/vinyl dimethicone crosspolymer (and) C12-14 Pareth-12). In some instances, the soft focus powder is (or includes) sodium acrylates crosspolymer-2, which is commercially available as AQUAKEEP 10SH-NFC as sodium acrylates crosspolymer-2 (and) water (and) silica.

The total amount of soft focus powder, if present, can vary but is typically about 0.1% to about 20%, by weight based on the total weight of the skin-tightening composition. In some cases, the total amount of soft focus powder is about 0.1% to about 15%, about 0.1% to about 10%, about 0.1% to about 5%, about 1% to about 20%, about 1% to about 15%, about 1% to about 10%, or about 1% to about 10%, by weight based on the total weight of skin-tightening composition.

Active Ingredients

The skin-tightening compositions described herein may, optionally, include one or more active ingredients. The compositions may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In one some instances, the skin-tightening composition includes an active ingredient such as a humectant and moisturizing ingredients, an anti-aging agent, a depigmenting agent, an anti-wrinkle agent, or an agent that treats oily skin.

Humectants and moisturizing ingredients may be glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract Prophyridium cruentum enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-0 ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, ferox, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-0 ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxy-propane as described in particular in EP-1345919, plant extracts including sea fennel and extracts of olive leaves, as well as plant and hydrolysates thereof such as rice protein hydrolysates or soybean proteins; algal extracts and in particular laminaria, bacterial extracts, the sapogenins such as diosgenin and extracts of Dioscorea plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

Water

The total amount of water in the skin-tightening composition can vary, but is typically about 30% to about 95, by weight based on the total weight of the skin-tightening composition. In some instances, total amount of water is about 30% to about 90%, about 30% to about 85%, about 30% to about 80.%, about 35% to about 90%, about 35% to about 85%, about 35% to about 80%, about 40% to about 90%, about 40% to about 85%, about 40% to about 80%, about 45% to about 90%, about 45% to about 85%, about 45% to about 80%, about 50% to about 90%, about 50% to about 85%, about 50% to about 80%, about 55% to about 90%, about 55% to about 85%, about 55% to about 80%, about 60% to about 90%, about 60% to about 85%, about 60% to about 80%, about 65% to about 90%, about 65% to about 85%, or about 65% to about 80%, including ranges and sub-ranges therebetween, by weight based on the total weight of the skin-tightening composition.

pH Adjuster(s)

The skin-tightening composition may include one or more pH adjusters to increase or decrease the overall pH of the skin-tightening composition. For example, one or more acids may be included to decrease the pH of the skin-tightening composition. Examples of suitable acids for decreasing the pH of the skin-tightening composition include, but are not limited to, citric acid, acetic acid, etc. The skin-tightening composition may include one or more bases, such as sodium hydroxide, potassium hydroxide etc., to decrease the pH of the skin-tightening composition. Additional or alternative acids and bases that are suitable for adjusting the pH of the skin-tightening composition are readily known to one of ordinary skill in the art.

The amount of the pH adjuster in the skin-tightening composition may be based on the desired pH of the final skin-tightening composition and/or product. For example, the total amount of the pH adjuster may range from about 0.05% to about 20%, based on the total weight of the skin-tightening composition. In some instances, the total amount of pH adjuster is from about 0.05% to about 15%, about 0.5% to about 10%, about 1% to about 5%, about 1.5% to about 4%, or about 2.0% to about 3%, by weight of the total weight of the skin-tightening composition, including ranges and sub-ranges therebetween. Additionally or alternatively, the skin-tightening compositions may include an amount of pH adjuster ranging from 0.05% to 15%, 0.5% to 10%, 1% to 5%, 1.5% to 4%, or 2.0% to 3%, by weight of the total weight of the skin-tightening composition, including ranges and sub-ranges therebetween.

The skin-tightening compositions disclosed herein may be in the form of a liquid dispersion, a gel, a cream, a lotion, a mousse, or a spray. The skin-tightening compositions may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form. Preferably, the skin-tightening compositions are in the form of an oil-in-water emulsion.

The instant disclosure also relates to methods for improving the appearance of skin by applying the skin-tightening compositions described herein to the skin. The methods may improve the appearance of skin by treating or reducing the appearance of, e.g., eye bags, wrinkles, blemishes, dryness, roughness, dullness, age spots, sagging, and/or puffy skin.

Additionally, the instant disclosure relates to methods for firming and/or tightening the skin by applying the skin-tightening compositions described herein to the skin and forming a skin-tightening film or layer on the skin. In some instances, the skin tightening compositions are applied to the skin of the face, and/or more specifically around the eyes, around the mouth, and/or around the neck.

The methods typically include application of the skin-tightening composition to the skin. For example, the compositions may be applied with the hands and simply spread or rubbed onto the skin. The compositions are particularly well suited for application to the skin of the face and/or neck, especially the skin around the eyes (for example, under the eyes and/or at the outer edges of the eyes where crow's feet typically form). The skin tightening effects of the skin-tightening compositions are long lasting. For instance, the skin tightening effects can last at least 2 hours, at least 3 hours, at least 4 hours, at least 5 hours, at least 6 hours, at least 7 hours, or at least 8 hours. The skin tightening effects occur immediately upon application to the skin. For instance, the skin tightening effects typically occur within 30 seconds of application to the skin, but may occur within 1 minutes, within 2 minutes, within 5 minutes, or within 10 minutes of application to the skin.

EMBODIMENTS

In certain embodiments, the skin-tightening compositions of the instant disclosure optionally form an oil-in-water emulsion and include:
- at least 1 to about 15 wt. %, preferably about 1.5 to about 10 wt. %, more preferably about 2 to about 7 wt. %, of one or more polyvalent silicates, such as those selected from magnesium aluminum silicate, magnesium silicate, calcium silicate, aluminum silicate, a polyvalent silicate clay, montmorillonite, bentonite, smectite, and a mixture thereof;
- about 1 to about 10 wt. %, preferably about 1 to about 8 wt. %, more preferably about 1.5 to about 5 wt. %, of one or more cellulose thickeners, such as those selected from hydroxyethylcellulose, hydroxymethylcellulose, hydroxypropylcellulose, methylcellulose, ethylhydroxyethylcellulose, carboxymethylcellulose, and a mixture thereof;
- about 1 to about 10 wt. %, preferably about 1 to about 8 wt. %, more preferably about 1.5 to about 5 wt. %, of one or more clays selected from hectorite and organically modified hectorites, the one or more clays optionally being selected from disteardimonium hectorite, stearalkonium hectorite, and a mixture thereof;
- about 0.1 to about 10 wt. %, preferably about 0.5 to about 8 wt. %, more preferably 0.8 to 6 wt. %, of one or more polysaccharide film forming agents, such as those selected from pullulan, galactoarabinan, xanthan gum, cellulose, cellulose derivatives, gellan gum, guars, carrageenan, pectin, and a mixture thereof; about 1 to about 25 wt. %, preferably about 2 to about 20 wt. %, more preferably about 3 to about 10 wt. %, of one or more polyols, the polyols preferably having from 2 to 15 carbon atoms and at least two hydroxyl groups;
- about 0.1 to about 10 wt. %, preferably about 0.1 to about 8 wt. %, more preferably about 0.1 to about 5 wt. %, of one or more acrylate polymers, such as those selected from acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof; and
- about 50 to about 90 wt. %, preferably about 55 to about 85 wt. %, more preferably about 65 to about 80 wt. %, of water, wherein the weight percentages are based on the total weight of the composition.

In additional embodiments, the skin-tightening compositions of the instant disclosure may include:
- at least 1 to about 15 wt. % preferably about 1.5 to about 10 wt. %, more preferably about 2 to about 7 wt. %, of magnesium aluminum silicate;
- about 1 to about 10 wt. %, preferably about 1 to about 5 wt. %, more preferably about 1.5 to about 4 wt. %, of one or more cellulose thickeners such as those selected from hydroxyethylcellulose, hydroxymethylcellulose, hydroxypropylcellulose, methylcellulose, ethylhydroxyethylcellulose, carboxymethylcellulose, and a mixture thereof;
- about 1 to about 10 wt. %, preferably about 1 to about 5 wt. %, more preferably about 1.5 to about 4 wt. %, of one or more clays selected from hectorite and organically modified hectorites, the one or more clays optionally being selected from disteardimonium hectorite, stearalkonium hectorite, and a mixture thereof;
- about 0.1 to about 10 wt. %, preferably about 0.5 to about 8 wt. %, more preferably 0.8 to 6 wt. %, of pullulan, galactoarabinan, or a mixture thereof; about 1 to about 25 wt. %, preferably about 3 to about 20 wt. %, more preferably about 4 to about 15 wt. %, of one or more polyols, the polyols preferably having from 2 to 15 carbon atoms and at least two hydroxyl groups, such as those selected from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

about 0.1 to about 10 wt. %, preferably about 0.1 to about 5 wt. %, more preferably about 0.1 to about 3 wt. %, of one or more acrylate polymers, such as those selected from acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof;

about 50 to about 90 wt. %, preferably about 55 to about 85 wt. %, more preferably about 65 to about 80 wt. %, of water;

one or more fatty compounds, preferably in an amount of about 0.1 to about 25 wt. %, more preferably about 1 about 10 wt. %, the one or more fatty compounds optionally being selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof; and about 0.1 to about 20 wt. %, preferably about 0.1 to about 6 wt. %, more preferably about 0.5 to about 4 wt. %, of one or more emulsifiers, such as those selected from polyglyeryl-based emulsifiers, polyol esters, glycerol ethers, oxyethylenated and/or oxypropylenated ethers, ethylene glycol polymers, sorbitan esters, and a mixture thereof. The weight percentages are based on the total weight of the composition.

EXAMPLES

The following non-limiting examples are provided primarily for the purposes of elucidating the benefits and properties achieved by aspects of the invention.

Example 1

In Example 1, thirteen skin-tightening compositions (Examples A-M) were prepared in accordance with the exemplary formulations provided in Table 1, shown on the following page. The skin-tightening compositions of Examples A-M all formed stable oil-in-water emulsions.

TABLE 1

| INCI US | A wt. % | B wt. % | C wt. % | D wt. % | E wt. % | F wt. % | G wt. % | H wt. % | I wt. % | J wt. % | K wt. % | L wt. % | M wt. % |
|---|---|---|---|---|---|---|---|---|---|---|---|---|---|
| (a) MAGNESIUM ALUMINUM SILICATE | 5 | 5 | 5 | 5 | 5 | 5 | 5 | 5 | 5 | 5 | 5 | 5 | 5 |
| (b) HYDROXYPROPYLCELLULOSE | 2 | 2 | 2.3 | 2.1 | 2.2 | 2.3 | 2 | 2 | 2 | 2 | 2 | 2 | 2 |
| (c) STEARALKONIUM HECTORITE | 2.3 | 3 | 2.5 | 2.6 | 2.6 | 2.4 | 3 | 3 | 3 | 3 | 3 | 3 | 3 |
| (d) PULLULAN and/or GALACTOARABINAN | 1 | 1 | 0.6 | 3.4 | 0.9 | 0.3 | 1 | 1 | 1 | 1 | 1 | 1 | 1 |
| (e) PENTYLENE GLYCOL, GLYCERIN, PROPYLENE GLYCOL, and/or CAPRYLYL GLYCOL | 5.3 | 5.3 | 5.3 | 5.3 | 5.3 | 5.3 | 5.3 | 13.6 | 5.6 | 5.3 | 5.3 | 5.3 | 5.4 |
| (f) SODIUM ACRYLATES COPOLYMER and/or ACRYLATES COPOLYMER | 0.8 | 0.8 | 0.8 | 0.8 | 0.8 | 0.8 | 0.8 | 0.8 | 0.8 | 0.8 | 0.8 | 0.8 | 1.7 |
| (h) CAPRYLIC/CAPRIC TRIGLYCERIDE | 2 | 2 | 2 | 2 | 2 | 2 | 2 | 2 | 2 | 2 | 2 | 2 | 2 |
| (i) POLYGLYCERYL-3 METHYLGLUCOSE DISTEARATE STEARETH-20, and/or LECITHIN | 1.2 | 1.2 | 1.2 | 1.2 | 1.2 | 1.2 | 1.2 | 1.3 | 1.3 | 1.2 | 1.2 | 1.2 | 1.2 |
| ACRYLATES/ POLYTRIMETHYLSILOXY-METHACRYLATE COPOLYMER | | | | | | | | | | | | 1 | |
| XANTHAN GUM | | | | | | | | | | 0.4 | 0.4 | 0.4 | 0.4 |
| MICA, IRON OXIDES, TIN OXIDE, AND/OR TITANIUM DIOXIDE | | | | | | 2.2 | | | | | | | |
| ISODODECANE | | | | | | | | | | | | 1.5 | |
| LICORICE ROOT EXTRACT, CAFFEINE, BIOTIN, AND/OR ADENOSINE | | | | | | | | 1.2 | 1.1 | | | | |
| PRESERVATIVES, CHELATING AGENTS, PH ADJUSTERS, ETC. | | ≤1 | | | | | ≤1 | ≤1 | ≤1 | ≤1 | ≤1 | ≤1 | ≤1 |
| (g) WATER | 80 | 79 | 80 | 77 | 81 | 80 | 77 | 69 | 78 | 77 | 78 | 76 | 77 |

Example 2

In Example 2, the skin-tightening compositions of Examples J-M were evaluated by applying each of the skin-tightening compositions to the section of skin around the eyes of the six respective individuals-namely the sections of skin where eye bags and crow's feet develop. An expert evaluation of eye bags was performed by an aesthetician using a 7 point scale atlas grading. The efficacy of the product was examined at the time of application of the skin-tightening compositions (T=0), 10 min, 30 min, 3 hours, and 6 hours after application of the respective skin-tightening compositions. The individuals had an average grade of 2 based on the Atlas scaling for eye bags before the application of the skin-tightening compositions, which was used as the baseline for determining the reduction of eye bags. The FIGURE illustrates the reduction in eye bags over time produced by the skin-tightening compositions of Examples J-M.

After application of the skin-tightening compositions of Examples J-M, an immediate tightening effect on the skin was observed. Example K produced a reduction in eye bags of about 1.7 based on the Atlas scaling. Desirably, Example K also resulted in a reduction of wrinkles in the skin under the eyes of 1.83 in 30 minutes. Example L produced a reduction in eye bags of about 1.5 that extended from the $10^{th}$ minute after the application of the skin-tightening composition to the $6^{th}$ hour after application of the skin-tightening composition. Example L also provided a reduction of wrinkles in the skin under the eyes. The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the cosmetic compositions of the instant disclosure can be free or essentially free of all components and elements positively recited throughout the instant disclosure.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular composition includes both a nonionic surfactant and a fatty compound, a single fatty acid will serve as only the nonionic surfactant or as only the fatty compound (the single fatty acid does not serve as both the nonionic surfactant and the fatty compound).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as skin, in particular, the skin of the head, face, and neck.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

The invention claimed is:

1. A skin-tightening composition in the form of an oil-in-water emulsion comprising:
    (a) at least 1 to about 15 wt. % of montmorillonite;
    (b) about 1 to about 10 wt. % of one or more cellulose thickeners;
    (c) about 1 to about 10 wt. % of one or more clays selected from hectorite and organically modified hectorites;
    (d) about 0.1 to about 10 wt. % of one or more polysaccharide film forming agents;
    (e) about 1 to about 25 wt. % of one or more polyols;
    (f) about 0.1 to about 10 wt. % of one or more acrylate polymers; and
    (g) about 50 to about 90 wt. % of water,
        wherein the weight percentages are based on the total weight of the composition.

2. The skin-tightening composition of claim 1, wherein the montmorillonite is a magnesium aluminum silicate, a aluminum silicate, or a mixture thereof.

3. The skin-tightening composition of claim 2, wherein the montmorillonite is a magnesium aluminum silicate.

4. The skin-tightening composition of claim 1, wherein the one or more cellulose thickeners are selected from hydroxyethylcellulose, hydroxymethylcellulose, hydroxypropylcellulose, methylcellulose, ethylhydroxyethylcellulose, carboxymethylcellulose, and a mixture thereof.

5. The skin-tightening composition of claim 1 comprising one or more organically modified hectorites selected from disteardimonium hectorite, stearalkonium hectorite, and a mixture thereof.

6. The skin-tightening composition of claim 1, wherein the one or more polysaccharide film forming agents are selected from pullulan, galactoarabinan, xanthan gum, cellulose, cellulose derivatives, gellan gum, guars, carrageenan, pectin, and a mixture thereof.

7. The skin-tightening composition of claim 6, wherein the one or more polysaccharide film forming agents comprise at least one of pullulan and galactoarabinan.

8. The skin-tightening composition of claim 1, wherein the one or more polyols are selected from polyols having from 2 to 15 carbon atoms and at least two hydroxyl groups.

9. The skin-tightening composition of claim 8, wherein the one or more polyols are selected from ethylene glycol, propylene glycol, butylene glycol, hexylene glycol, pentylene glycol, 1,3-propanediol, diethylene glycol, dipropylene glycol, caprylyl glycol, glycerin, and a mixture thereof.

10. The skin-tightening composition of claim 1, wherein the one or more acrylate polymers is selected from acrylates copolymer, styrene/acrylates copolymer, acarylates/ethylhexyl acrylate copolymer, an alkyl acrylate copolymer, acrylic copolymers, polyacrylate-2 crosspolymer, acrylates/hydroxyesters acrylate copolymer, acrylate/ethylhexyl acrylate copolymer, styrene acrylate copolymer, acrylate/VA copolymer, styrene/acrylic copolymer, styrene/acrylates copolymer, styrene/acrylates/ammonium methacrylate copolymer, and a mixture thereof.

11. The skin-tightening composition of claim 1, further comprising:
(h) one or more fatty compounds.

12. The skin-tightening composition of claim 1, wherein the one or more fatty compounds are selected from fatty acid triglycerides, oils, mineral oil, alkanes, fatty alcohols, fatty acids, fatty alcohol derivatives, alkoxylated fatty acids, polyethylene glycol esters of fatty acids, propylene glycol esters of fatty acids, butylene glycol esters of fatty acids, esters of neopentyl glycol and fatty acids, polyglycerol/glycerol esters of fatty acids, glycol diesters, diesters of ethylene glycol and fatty acids, esters of fatty acids and fatty alcohols, esters of short chain alcohols and fatty acids, esters of fatty alcohols, hydroxy-substituted fatty acids, waxes, and a mixture thereof.

13. The skin-tightening composition of claim 1, wherein the one or more fatty compounds include one or more fatty acid triglycerides.

14. A method for improving the appearance of skin comprising applying the skin-tightening composition of claim 1 to the skin.

15. A method for firming and/or tightening the skin comprising applying the composition of claim 1 to the skin.

16. The skin tightening composition of claim 1 being free of sodium silicate.

17. The skin-tightening composition comprising (i) about 0.1 to about 20 wt. % of one or more emulsifiers.

18. A skin-tightening composition comprising:
(a) at least 1 to about 15 wt. % of magnesium aluminum silicate;
(b) about 1 to about 10 wt. % of one or more cellulose thickeners;
(c) about 1 to about 10 wt. % of one or more clays selected from hectorite and organically modified hectorites;
(d) about 0.1 to about 10 wt. % of pullulan, galactoarabinan, or a mixture thereof;
(e) about 1 to about 25 wt. % of one or more polyols;
(f) about 0.1 to about 10 wt. % of one or more acrylate polymer;
(g) about 50 to about 90 wt. % of water;
(h) one or more fatty compounds; and
(i) about 0.1 to about 20 wt. % of one or more emulsifiers, wherein the weight percentages are based on the total weight of the composition.

19. The skin tightening composition of claim 18 being free of sodium silicate.

\* \* \* \* \*